US008101701B2

(12) United States Patent
Itoh et al.

(10) Patent No.: US 8,101,701 B2
(45) Date of Patent: Jan. 24, 2012

(54) FUMARIC ACID DERIVATIVES AND OPHTHALMIC LENSES USING THE SAME

(75) Inventors: Takahito Itoh, Tsu (JP); Takahiro Uno, Tsu (JP); Masato Ohnishi, Tsu (JP); Yasuyuki Kato, Nagoya (JP); Takashi Otsu, Nagoya (JP)

(73) Assignees: Menicon Nect Co., Ltd., Nagoya-shi (JP); Mie University, Mie-ken (JP)

( * ) Notice: Subject to any disclaimer, the term of this patent is extended or adjusted under 35 U.S.C. 154(b) by 720 days.

(21) Appl. No.: 11/766,857

(22) Filed: Jun. 22, 2007

(65) Prior Publication Data
US 2008/0132666 A1 Jun. 5, 2008

(30) Foreign Application Priority Data

Dec. 1, 2006 (JP) ................................. 2006-357020

(51) Int. Cl.
C08F 26/06 (2006.01)
C08F 230/08 (2006.01)
G02C 7/02 (2006.01)
(52) U.S. Cl. ........ 526/279; 526/258; 351/159; 548/406; 562/400; 556/437; 556/442
(58) Field of Classification Search ................. 351/159; 548/406, 430; 562/400; 556/437, 442; 526/258, 526/279
See application file for complete search history.

(56) References Cited

U.S. PATENT DOCUMENTS 5,374,662 A * 12/1994 Lai et al. ................. 522/172
5,786,434 A * 7/1998 Ando et al. .............. 526/264

FOREIGN PATENT DOCUMENTS

| JP | 58-18335 | 2/1983 |
|---|---|---|
| JP | 60-181047 | 9/1985 |
| JP | 2-50450 | 11/1990 |
| JP | 4-335007 | 11/1992 |
| JP | 04335006 A | * 11/1992 |
| JP | 6-25832 | 4/1994 |
| JP | 6-77115 | 9/1994 |
| JP | 6-85030 | 10/1994 |
| JP | 8-23630 | 3/1996 |
| JP | 9-77861 | 3/1997 |
| JP | 3050586 | 3/2000 |
| JP | 3227811 | 9/2001 |
| JP | 3240696 | 10/2001 |
| JP | 2002-265417 | 9/2002 |
| JP | 3453224 | 7/2003 |
| JP | 3612349 | 10/2004 |
| WO | WO 97/08177 | 3/1997 |
| WO | WO 01/60780 A1 | 8/2001 |

OTHER PUBLICATIONS

Abstract in English, JP-04335006, Koinuma et al, Nov. 1992.*

* cited by examiner

Primary Examiner — Karuna P Reddy
(74) Attorney, Agent, or Firm — Antonelli, Terry, Stout & Kraus, LLP.

(57) ABSTRACT

Fumaric acid derivatives and ophthalmic lenses using them are disclosed. More specifically, a fumaric acid derivative having a hydrophilic group and a silicon-containing alkyl group within a molecule, and contact lenses or intraocular lenses using the same are disclosed. The fumaric acid derivatives of the present invention provide, on one hand, superior oxygen permeability by having a silicon-containing alkyl group within the molecular structure, and on the other hand, improved compatibility with other hydrophilic monomers by having a hydrophilic group within the same molecule. When ophthalmic lenses obtained by polymerizing monomer compositions containing the fumaric acid derivative are constructed as, for example, water content lenses, lenses with high oxygen permeability independent from the water content may be obtained, wherein the fumaric acid derivatives is superior in compatibility with the hydrophilic monomer used in combination and allows the combination in various mixing ratios.

4 Claims, 1 Drawing Sheet

FUMARIC ACID DERIVATIVES AND OPHTHALMIC LENSES USING THE SAME

BACKGROUND OF THE INVENTION

The present invention relates to fumaric acid derivatives and ophthalmic lenses using them. More specifically, the present invention relates to a fumaric acid derivative having a hydrophilic group and a silicon-containing alkyl group within a molecule, and to contact lenses or intraocular lenses using the same.

In the field of medical materials, particularly for ophthalmic lenses, such as contact and intraocular lenses, a variety of monomers have been investigated for use as such materials. Among them, fumaric acid esters, which exhibit advantageous properties, including transparency, mechanical strength and oxygen permeability, when they are processed into lenses, have conventionally been proposed more often than other materials. These properties are considered indispensable for the materials for ophthalmic lenses, because such lenses are applied in direct contact with the living body.

Fumaric acid is a white crystalline powder and has a wide range of industrial applications, including food additives, materials for pharmaceutical products and bath agents. In its chemical structure, two carboxyl groups are located on the both ends of an unsaturated bond of hydrocarbon group. It has been studied as fumaric acid ester contact lens material monomers by introducing a variety of substituents into the carboxyl groups through an ester bond. For example, dialkyl fumarates having a hydrophobic alkyl group, such as linear or branched alkyl or cycloalkyl, as a substituent are disclosed, for example, in JP 02-50450B, JP 06-85030B, and JP 08-23630B, and those having an hydrophilic substituent, such as a phosphorylcholine or hydroxyalkyl group, are disclosed, for example, in Japanese Patent Nos. 3240696, 3227811 and 3612349. Di-(silicon-containing alkyl)fumarates are disclosed, for example, in JP 06-77115B, Japanese Patent Nos. 3050586 and 3453224. Di-(fluoroalkyl)fumarates are disclosed in Japanese Patent No. 3050586.

The above-mentioned fumarates are all of a so-called symmetrical type, in which the substituents are basically identical. This type of fumarates is synthesized primarily for the purpose of improving the oxygen permeability and, in fact, they exhibit superior properties. On the other hand, as partially disclosed in the foregoing patent publications, asymmetrical types of fumarates, in which the substituents are different from each other, have also been investigated. For example, fumarates having silicon-containing alkyl and fluoroalkyl groups (JP 06-25832B, etc.), those having a linear, branched or cyclic alkyl group and a polyoxyethylene chain (JP 04-335007A, etc.), and those having an alkyl group with 1-20 carbon atoms and phosphorylcholine (WO 97/08177) have been used for contact lenses.

These fumarates have been developed for the purpose not only of enhancing the required oxygen supply to the cornea, but also of possessing moderate wettability, transparency as an optical material, biocompatibility and resistance to deposits.

Meanwhile, despite their ability to provide lens materials with good oxygen permeability, the fumaric acid esters proposed in the foregoing patent publications remain minor in the market at present, compared to the lens materials using silicon-containing methacrylates or polydimethylsiloxane macromers. In the field of contact lenses, there are oxygen permeable hard lenses, water-containing soft contact lenses, and silicone hydrogel contact lenses, which recently became commercially available. For oxygen permeable hard lenses and silicone hydrogel contact lenses, silicon-containing methacrylates or macromers as mentioned above are used, and acrylamide monomers, N-vinyl lactams, 2-hydroxymethyl methacrylates, methacrylic acid, and such are used for water-containing soft contact lenses.

One of the reasons why lenses actually employing fumaric acid esters are difficult to make commercially viable is that while the material cost of using a fumaric acid ester alone is high, there is a problem of compatibility between monomers if the fumaric acid ester is used in combination with other general-purpose monomers, although such specifying the reason is not necessarily proper. Specifically, use of a large amount of a fumaric acid ester having a silicon-containing alkyl group as a substituent is desirable on one hand for improving the oxygen permeability, and on the other hand, copolymerization of hydrophilic monomers is required for ensuring moderate wettability of the lens materials. However, since silicon-containing alkyl fumarates generally have poor compatibility with hydrophilic monomers, their use is restricted to a limited composition ratio. Furthermore, when obtaining water-containing soft contact lenses, there often occur problems, such as, in particular, white turbidity after hydration, due to the difficulty in obtaining homogenous polymers because of the difference in polymerization reactivity between monomers used in combination, in addition to the intrinsic problem in their compatibility.

In view of the prior art described above, the inventors have made the present invention. Objectives of the present invention are to provide novel fumaric acid derivatives that may improve the compatibility with other monomers used in combination, in particular, hydrophilic monomers, by taking advantage of the superior features of the fumaric acid derivative monomers, including transparency, mechanical strength and oxygen permeability, and to provide ophthalmic lenses, such as contact lenses or intraocular lenses, using such derivatives.

SUMMARY OF THE INVENTION

As a result of extensive research to achieve the above-mentioned objective, the inventors have found that the objective may be achieved by introducing a hydrophilic substituent group into one of the carboxyl groups and a silicon-containing alkyl group into the other carboxyl group, and have completed the present invention.

More specifically, the present invention relates to a fumaric acid derivative represented by formula (1):

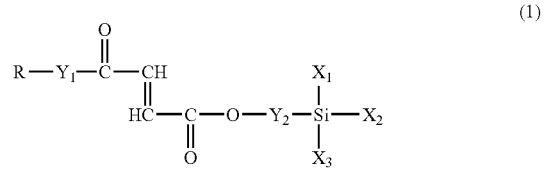

which has a hydrophilic group (R) and a silicon-containing alkyl group, and to ophthalmic lenses obtained by polymerizing the fumaric acid derivative, wherein $Y_1$ is O or $NR_1$ ($R_1$ is selected from the group consisting of hydrogen, $C_{1-3}$ alkyl and aryl);

R is selected from the group consisting of —$(CH_2CH_2O)_m$-A (m is an integer from 1 to 10; A represents methyl or ethyl), and the groups represented by the following formulae:

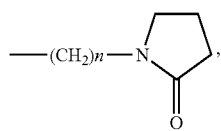
(n is an integer from 1 to 3)

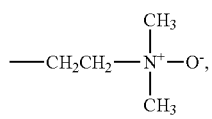  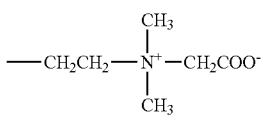

$Y_2$ is linear or branched $C_{3-10}$ alkylene, phenylene, cyclohexylene, —$(CH_2CH_2O)_o$—$CH_2CH_2CH_2$— (o is an integer from 1 to 10), or a group represented by any one of the following formulae:

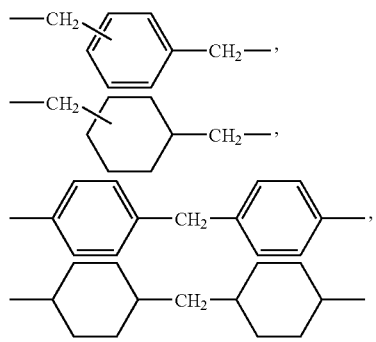

$X_1$, $X_2$ and $X_3$ are independently selected from methyl, trimethylsiloxy, and organosiloxy with 18 Si atoms or less.

The fumaric acid derivatives of the present invention provide, on one hand, superior oxygen permeability by having a silicon-containing alkyl group in its molecular structure, and on the other hand, improved compatibility with other hydrophilic monomers by having a hydrophilic group within the same molecule. Ophthalmic lenses obtained by polymerizing monomer compositions containing the fumaric acid derivative may form lens materials having not only high oxygen permeability but also high surface hydrophilicity, when constructed as hard lenses, and may exhibit good compatibility with hydrophilic monomers used in combination, may be combined with hydrophilic monomers at various composition ratios, and may satisfy the high oxygen permeability requirement independent from the water content, when constructed as water-containing soft contact lenses.

DETAILED DESCRIPTION

Figure 1:
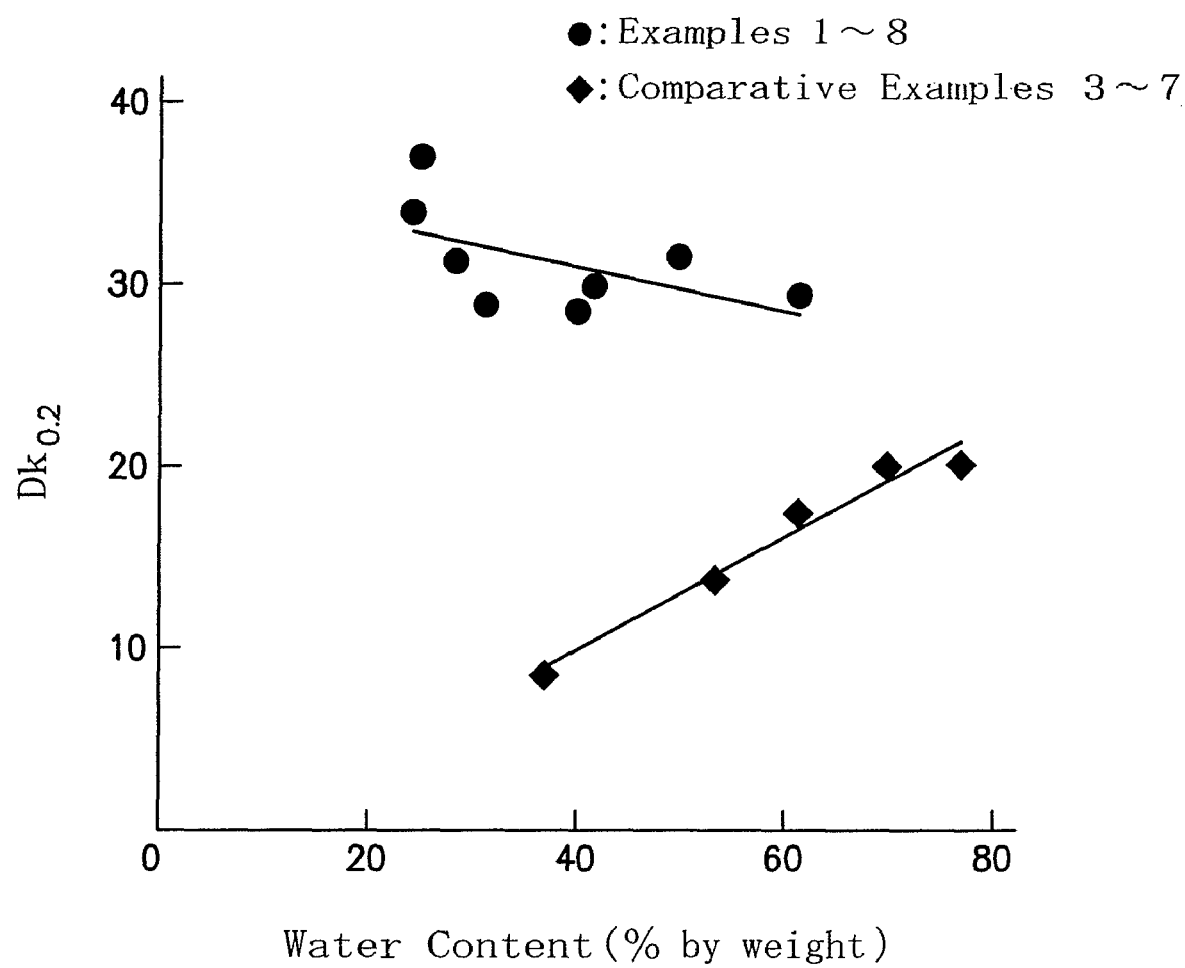
FIG. 1 is a graph showing the relationships between the water content and oxygen permeability described in Examples 1 to 8 and Comparative Examples 3 to 7.

The fumaric acid derivatives of the present invention and synthesis thereof are described in greater detail hereinbelow. The fumaric acid derivatives of the present invention are represented by the formula (1):

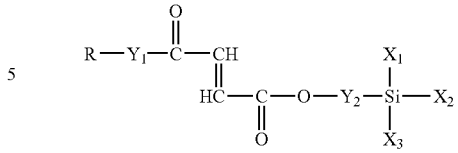

(1)

wherein $Y_1$ is O or $NR_1$ ($R_1$ is selected from the group consisting of hydrogen, $C_{1-3}$ alkyl and aryl);

R is selected from the group consisting of —$(CH_2CH_2O)_m$-A (m is an integer from 1 to 10; A represents, methyl or ethyl), and the groups represented by the following formulae:

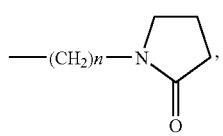

(n is an integer from 1 to 3)

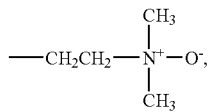  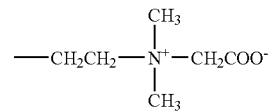

$Y_2$ is linear or branched $C_{3-10}$-alkylene, phenylene, cyclohexylene, —$(CH_2CH_2O)_o$—$CH_2CH_2CH_2$— (o is an integer from 1 to 10), or a group represented by any one of the following formulae:

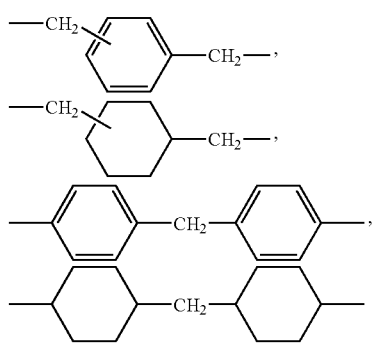

$X_1$, $X_2$ and $X_3$ are independently selected from methyl, trimethylsiloxy, and organosiloxy groups with 18 Si atoms or less.

R—$Y_1$— in the formula (1) represents a hydrophilic substituent introduced into one of the carboxyl groups of fumaric acid. The introduction of a hydrophilic substituent is performed by means of an ester bond with an alcohol, when $Y_1$ is oxygen (O), or by forming an amide bond with a primary or secondary amine, when $Y_1$ is —$NR_1$—. Although this ester or amide bond per se imparts a certain level of hydrophilicity to the compound, subsequent introduction of the substituent R further improves the hydrophilicity.

Examples of the —$(CH_2CH_2O)_m$-A group (m is an integer from 1 to 10; A represents, methyl or ethyl) include diethylene glycol, triethylene glycol, tetraethylene glycol, nonaethylene glycol, 2-methoxyethylene, 2-ethoxyethylene, diethylene glycol methyl ether, and triethylene glycol methyl ether. In particular, 2-hydroxyethyl, 2-methoxyethylene, diethylene glycol, (2-methoxyethoxy)ethylene, triethylene glycol, and [2-(2-methoxyethoxy)ethoxy]ethylene are preferred for the reasons of facilitating the synthetic reaction and of simplifying the purification process. These are easy to obtain as commercially available products and serve to reduce the cost.

$Y_2$ in the formula (1) represents the group linking the carboxyl group of fumaric acid to the silicon-containing alkyl group. In the formula, the linear or branched $C_{3-10}$-alkylene includes propylene, n-butylene, pentylene, hexylene, isopropylene and isobutylene. In addition to these groups, $Y_2$ may be phenylene, cyclohexylene, —$(CH_2CH_2O)_o$—$CH_2CH_2CH_2$— (o is an integer from 1 to 10), or a group represented by any one of the following formulae:

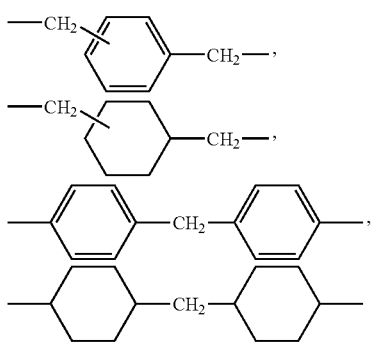

Since in general, these groups are introduced simultaneously into fumaric acid by binding to the silicon-containing alkyl group, they are conveniently determined simultaneously with the selection of the silicon-containing alkyl group. Typically, $Y_2$ is a propylene group, which is easy to obtain.

$X_1$, $X_2$ and $X_3$ in the formula (1) are independently methyl, trimethylsiloxy, and organosiloxy groups with 18 Si atoms or less, such as pentamethyldisiloxy, methylbis(trimethylsiloxy)siloxy, tris(pentamethylsiloxy)siloxy, trimethylsiloxydimethylsiloxy, methylbis(trimethylsiloxy)siloxy, mono[methylbis(trimethylsiloxy)siloxy]bis(trimethylsiloxy)siloxy, tris[methylbis(trimethylsiloxy)siloxy]siloxy, mono[methylbis(trimethylsiloxy)siloxy]bis(trimethylsiloxy)siloxy, nonamethyltetrasiloxy, pentadecamethylheptasiloxy, heptacosamethyltridecasiloxy, tris(pentamethyldisiloxy)siloxy, nonamethyltetrasiloxyundecylmethylpentasiloxy, and nonakis(trimethylsiloxy)tetrasiloxy. The terminal hydrogen of the organosiloxy group may be replaced with alkyl group, such as methyl, ethyl, butyl, and amyl group, or alkyl group in which hydrogen is replaced by fluorine. Among the above exemplified groups, trimethylsiloxy is preferred for its ease of obtaining.

By way of example, the fumaric acid derivatives of the present invention may be synthesized by the following reactions. Initially, ring-opening addition reaction is conducted between maleic acid anhydride and alcohol or polyalcohol having a substituent desired to be introduced as a hydrophilic substitutent, thereby obtaining maleic acid monoester. The maleic acid monoester thus obtained is then isomerized to fumaric acid monoester in the presence of thionyl chloride, and the fumaric acid monoester is further chlorinated (see, for example, JP 09-77861A and JP 2002-265417 A). The fumaric acid monoester chloride thus obtained is reacted with alcohol having silicon-containing alkyl group of interest to synthesis the fumaric acid diester of interest.

More specifically, the synthetic pathway represented by the following reaction formulae may be employed:

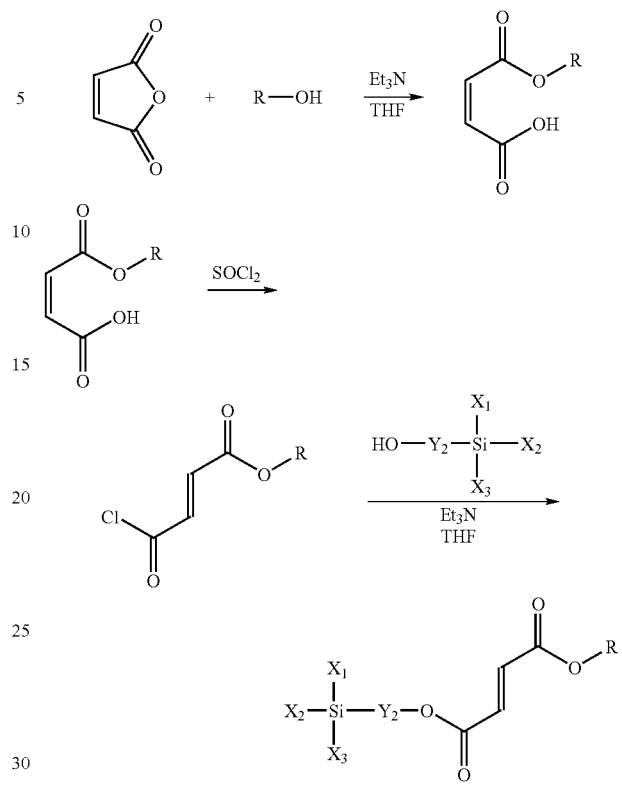

Examples of the alcohol or polyalcohol mentioned above include alcohols, such as 2-methoxyethanol, 2 (2-methoxyethoxy)ethanol, 2-[2-(2-methoxyethoxy)ethoxy]ethanol, 1-methoxy-2-propanol, 2(2-methoxypropoxy)propanol, 3-methoxy-3-methyl-1-butanol, 4-methoxy-4-methyl-2-pentanol, methoxyphenol, 2-methoxy-4-methylphenol, 4-methoxybenzylalcohol, 2-ethoxyethanol, 2(2-ethoxyethoxy)ethanol, 2-(dimethylamino)ethanol, and 2-(2-oxopyrrolidinyl)ethanol; and, in addition, polyalcohols, such as ethylene glycol, propylene glycol, diethylene glycol, dipropylene glycol, 1,3-butanediol, 1,4-butanediol, and 1,6-hexanediol. Amines, such as 2-methoxyethylamine and 3-methoxybutylamine, are used to form an amide bond with maleic acid anhydride for accomplishing the ring-opening addition reaction. In particular, 2-methoxyethanol, 2(2-methoxyethoxy)ethanol, 2-[2-(2-methoxyethoxy)ethoxy]ethanol and hydroxyethylpyrrolidone are preferred for ease of obtaining and cost reason.

The ring-opening addition reaction of maleic acid anhydride proceeds with ease, and the alcohols and such are desirably used in a molar ratio ranging from 0.8 to 1.2 mol, and preferably ranging from 0.9 to 1.1 mol per mol of maleic acid anhydride. This is because the yield of the reaction is reduced at a molar ratio of less than 0.8, while a molar ratio of more than 1.2 often causes side reactions. The reaction temperature ranging from 40 to 150° C. and the reaction time ranging from 1 to 6 hours are preferred. This is because the reaction proceeds slowly when the temperature is lower than this range, while the side reactions tend to occur when the temperature is higher than this range. To make this reaction proceed uniformly, it is preferable to use a reaction solvent, such as tetrahydrofuran, toluene, benzene, acetone, ethyl acetate, diethyl ether and isopropyl ether, and a reaction catalyst, such as a tertiary amine including triethylamine, in appropriate amounts.

Next, the thionyl chloride used for the isomerization is also used in the later step of chlorinating the maleic acid monoester. The amount used in these reactions is preferably in the range of 2 to 10 mol, and more preferably in the range from 3 to 5 mol per mol of the maleic acid monoester. This is because the yield of the reaction is reduced at a molar ratio of less than 2, while a molar ratio of more than 10 often causes side reactions. The reaction temperature ranging from 20 to 110° C. and the reaction time ranging from 1 to 6 hours are preferred. This is because the reaction proceeds slowly when the temperature is lower than this range, while the side reactions tend to occur when the temperature is higher than this range.

After fumaric acid monoester chloride has thus been obtained, excess thionyl chloride is eliminated, if necessary, from the reaction system by distillation, such as vacuum distillation. Subsequently, in order to introduce the other substituent, the silicon-containing alkyl group, an alcohol having silicon-containing alkyl group is added which is provided for reacting with the acid chloride.

Specific examples of such an alcohol having silicon-containing alkyl group includes, in addition to 2-trimethylsilylethanol, 3-trimethylsilylpropanol, 3-pentamethyldisiloxanylpropanol, 3-heptamethyltrisiloxanylpropanol, 3-bis(trimethylsiloxy)silylpropanol, 3-tris(trimethylsiloxy)silylpropanol, 4-tris(trimethylsiloxy)silylbutanol, 5-tris(trimethylsiloxy)silylpentanol, 3-tris(trimethylsiloxy)silylpropyl-3-phenol and 3-tris(trimethylsiloxy)silylpropyl-3-cyclohexanol, compounds having a terminal hydroxyl group at the 3-tris(trimethylsiloxy)silylpropyl group via the —(CH$_2$CH$_2$O)$_o$—CH$_2$CH$_2$CH$_2$— group (o is an integer from 1 to 10), or a group represented by any one of the following formulae:

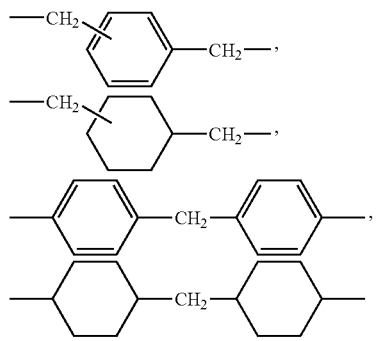

Among them, 3-tris(trimethylsiloxy)silylpropanol is particularly preferred, although others may be conveniently selected in consideration of the desired oxygen permeability, material cost, etc.

When adding the alcohol having silicon-containing alkyl group and being provided for reacting with the acid chloride, it is preferred to add a solvent in order to make the reaction uniform, and to add a tertiary amine as a catalyst. Examples of such a solvent include tetrahydrofuran, benzene, toluene, hexane, acetone, ethyl acetate, diethyl ether, isopropyl ether, chloroform, and methylene chloride. Examples of such a tertiary amine include triethylamine. The amount of the tertiary amine used is desirably within the range of 1.0 to 2.0 mol, and more preferably within the range of 1.2 to 1.5 mol per mol of fumaric acid chloride.

The mixing ratio between the acid chloride and the alcohol having silicon-containing alkyl group is preferably within the range from 0.5 to 1.5 mol of the alcohol per mol of the acid chloride. This is because there may occur a problem of reducing the production level of the compound of interest when the mixing ratio is higher than 1.5 or lower than 0.5. The reaction temperature is in the range of −10 to 20° C., preferably in the range of 0 to 5° C. The reaction time is in the range of 1 to 6 hours, preferably in the range of 1 to 2 hours.

The methods for isomerization include, in addition to the above-mentioned method using thionyl chloride, methods in which a halogen, such as fluorine, chlorine, bromine and iodine; an organic acid, such as p-toluenesulfonic acid; a base, such as acetylchloride, benzenesulfonylchloride, piperidine, morpholine, diethylamine; a phosphorus compound, such as triethylphosphate and triphenylphosphine; or thiourea is used as a cis-trans isomerization catalyst (see JP 58-18335A); methods using a quaternary ammonium, such as tetramethylammonium bromide and tetraethylammonium bromide (see JP 60-181047A); and methods using ruthenium, rhodium, palladium, iridium and platinum as an isomerization catalyst (see Republication WO 01/060780). Other examples include methods using transesterification, in which an alkali metal, such as lithium and sodium, or an organic metal compound, such as dibutyltin oxide and dibutyltin diacetate, is used as a catalyst (see JP 09-255622A). Although the method to be employed may be selected by considering the yield and production cost of fumaric acid ester of interest, the method using thionyl chloride is more convenient for synthesizing the asymmetric fumaric acid diesters of the present invention due to the reasons that fumaric acid chloride has high solubility in solvents and that the subsequent esterification or amidation reaction can be conducted in a homogeneous system.

The fumaric acid diester obtained by the above procedure may be used as an ophthalmic lens material for contact lenses and intraocular lenses by combining with another copolymerizable monomer. In the following description, the present invention is explained taking contact lens materials as example. It should be understood that the materials may also be used for intraocular lenses.

It is considered that contact lenses have use as oxygen permeable hard contact lenses, water-containing soft contact lenses, and others. Other monomers to be used in combination and composition ratios differ depending on the use of the lens material. For either use, it is preferable to use, in addition to the fumaric acid diesters of the present invention, a polyfunctional (meth)acrylate as a crosslinking agent, in order to ensure the mechanical strength as lenses and to prevent elution of unreacted monomers. Specifically, polyfunctional (meth)acrylates include ethylene glycol di(meth)acrylate, diethylene glycol di(meth)acrylate, triethylene glycol di(meth)acrylate, allyl(meth)acrylate, diallyl phthalate, trimethylol propane trimethacrylate and divinyl benzene. Preferably, one or more of these are selected for use. The amount of the crosslinking agent to be used is preferably is in the range of 0.01 to 10 part by weight per 100 parts by weight of the total monomer mixtures.

When used as hard contact lenses, the lens materials include, in addition to the fumaric acid diesters of the present invention, fluoro-substituted alkyl(meth)acrylate which is monomer component copolymerizable therewith, such as trifluoroethyl(meth)acrylate, tetrafluoroethyl(meth)acrylate, pentafluoropropyl(meth)acrylate, hexafluoropropyl(meth)acrylate and hexafluorobutyl(meth)acrylate. Preferably, one or more of these are selected for use. These fluorinated monomers are conventionally known as components useful for preventing adhesion of contaminants. The amount of the monomer components to be used is typically added in a ratio of 0 to 50% by weight of the total monomers.

In order to improve the hardness and mechanical strength of contact lenses, a methacrylate monomer, such as methylmethacrylate, ethylmethacrylate and t-butylmethacrylate, or an aromatic vinyl monomer, such as styrene, t-butylstyrene, and α-methylstyrene, is used. Preferably, one or more monomers selected from these monomers are used. These monomers are typically added in a ratio of 0 to 30% by weight of the total monomers.

Furthermore, conventionally known organic siloxane monomers may be used which do not reduce the oxygen permeability if they are used in combination with a fumaric diester. Specifically, such monomers include trimethylsilylmethyl(meth)acrylate, pentamethyldisiloxanyl methyl(meth)acrylate, tris(trimethylsiloxy)silylethyl(meth)acrylate, tris(trimethylsiloxy)silylpropyl(meth)acrylate, methylbis(trimethylsiloxy)silylethyl(meth)acrylate, tris(pentamethyldisiloxanyloxy)silylpropyl(meth)acrylate and α,ω-(3-methacryoxypropyl)polydimethylsiloxane. Preferably, one or more monomers selected from these monomers are used. These monomers are typically added in a ratio of 0 to 50% by weight of the total monomers.

Additionally, to improve tear wettability of lens surface, or to obtain water-containing contact lenses, other hydrophilic monomers may be used. Specifically, such monomers include (meth)acrylic acid, 2-hydroxyethyl(meth)acrylate, 2-hydroxypropyl(meth)acrylate, glycerol(meth)acrylate, (meth)acrylamide, N,N-dimethylacrylamide, N,N-dimethylaminoethyl acrylate, N,N-dimethylaminoproply acrylamide, N-vinyl pyrrolidone, fumaric acid diesters, fumaric acid diamides, fumaric acid amide esters and N-vinyl lactams. Preferably, one or more monomers selected from these monomers are used. In general, monomers having a silicon-containing alkyl group as a substituent have poor compatibility with hydrophilic monomers, which often hinders unrestricted combination of such monomers. By contrast, the fumaric acid diesters of the present invention, which have a silicon-containing alkyl group at one substituent position and a hydrophilic group at the other substituent position, are free from the problem of compatibility if mixed with hydrophilic monomers, and they may be mixed with hydrophilic monomers in a wider range of composition ratio than ever before.

In this regard, in the case of hard contact lenses, the amount of the hydrophilic monomers used is preferably reduced to 5-30% by weight of the total monomers, while in the case of water-containing soft contact lenses, the amount is preferably set to a range of 30-70% by weight of the total monomers. Any of the above-mentioned monomers that can be used for hard contact lenses may be used in combination, even when used as water-containing soft contact lenses. For water-containing soft contact lenses, the proportion of hydrophilic monomers is relatively high, while for hard contact lenses, the proportion of the components other than the hydrophilic monomers is relatively high.

In sum, where obtaining hard contact lenses is attempted, the fumaric acid diester of the present invention is included in a ratio ranging from 10 to 80% by weight, preferably from 15 to 70% by weight, hydrophilic monomers are included in a ratio ranging from 5 to 30% by weight, and the other monomers are included in a ratio ranging from 10 to 60% by weight. In contrast, where obtaining water-containing soft contact lenses is attempted, the fumaric acid diester of the present invention is included in a ratio ranging from 5 to 70% by weight, preferably from 10 to 50% by weight, hydrophilic monomers are included in a ratio ranging from 30 to 60% by weight, and the other monomers are included in a ratio ranging from 0 to 50% by weight.

In addition, to the monomer mixture formulated as noted above, one or more polymerization initiators, including radical polymerization initiators, such as azobisisobutyronitrile, azobisdimethylvaleronitrile and benzoylperoxide, and photopolymerization initiators, such as benzoin methyl ether, benzoin ethyl ether, benzoin isobutyl ether, p-isopropyl-α-hydroxy isobutylphenone, N,N-tetraethyl-4,4-diaminobenzophenone and benzophenone, are selected and added in about 0.001 to 5 part by weight, preferably 0.01 to 2 part by weight per 100 parts by weight of the total monomer mixtures.

The monomer mixture thus prepared is molded in a container suitable for polymerization or a mold having a contact lens shape, and then formed as a polymer. Since there are a variety of gauges required for hard contact lenses, the materials are usually polymerized into a bar or block, and then finished into desired contact lenses by cutting and polishing. On the other hand, in most of the case of soft contact lenses, since there are one to several fundamental base curves and only a few gauges, the materials are often polymerized by molding. The molded lenses thus obtained are subjected, if necessary, to processing, such as surface-processing and hydration, and finished into products of interest.

Furthermore, to the contact lenses of the present invention, any colorant and ultraviolet absorber conventionally known in the art may be added in accordance with the intended use.

EMBODIMENTS

The present invention is specifically illustrated below with reference to several working examples.

Synthesis of Compound 1
(2-methoxyethyl-3-tris(trimethylsiloxy)silylpropyl fumarate)

The fumaric acid diester of the present invention (compound 1) may be obtained according to the following reaction formulae:

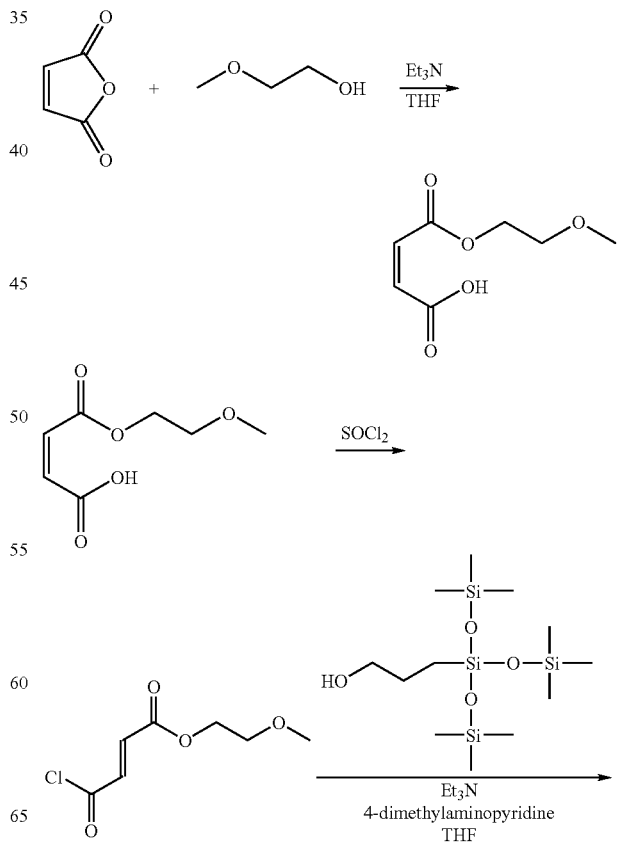

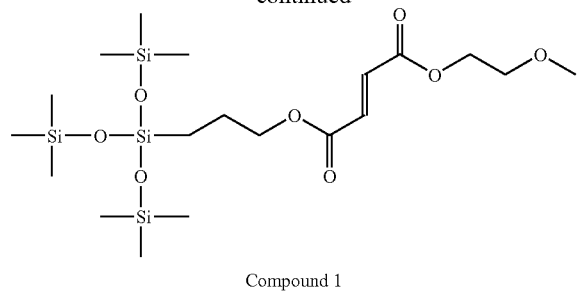

Compound 1

The synthesis was initiated by mixing 5.0 g (51 mmol) of maleic acid anhydride with 3.9 g (51 mmol) of 2-methoxyethanol, and dissolving the mixture by adding 30 ml of tetrahydrofuran (hereinafter referred to as "THF"). Then, 73 mg (0.72 mmol) of triethylamine (hereinafter referred to as "Et$_3$N") was added to the mixture and allowed to react for 2 hours at 70° C. A mixed solvent of ether/THF was added to the reaction solution for extraction, which was then dried over magnesium sulfate, and the solvent was distilled off.

The 2-methoxyethyl maleate thus obtained (6.5 g (37 mmol)) was added to 10 ml of thionyl chloride (hereinafter referred to as "SOCl$_2$"), and the mixture was heated to reflux for 1 hour under nitrogen atmosphere, and the excess SOCl$_2$ was distilled off over a period of 1 hour. To this mixture, 120 ml of THF and 7.9 g (22 mmol) of 3-tris(trimethylsiloxy) silylpropyl alcohol was added and dissolved, and the mixture was then allowed to react for 1 hour under cooling in the ice bath by adding 250 mg (2.2 mmol) of 4-dimethylaminopyridine and subsequently 7.5 g (74 mmol) of Et$_3$N. Subsequently, 1N hydrochloric acid was added to neutralize the solution, which was then extracted with 100 ml of ether, dried over magnesium sulfate, and the solvent was distilled off. Compound 1 of interest was obtained after vacuum distillation. The yield was 62%.

$^1$H- and $^{13}$C-nuclear magnetic resonance spectra of Compound 1 were measured using Model JNMα-400 (JAPAN ELECTRON OPTICS LABORATORY Co., LTD) in deuterated chloroform at 25° C. with 8 cumulative measurements for $^1$H-nuclear magnetic resonance spectrum and 128 cumulative measurements for $^{13}$C-nuclear magnetic resonance spectrum.

The results are as shown below:

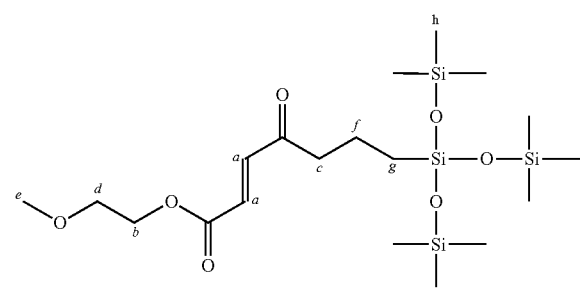

$^1$H NMR (CDCl$_3$), δ, ppm a) 6.89 (s, 2H) b) 4.37-4.33 (m, 2H) c) 4.14 (t, J=6.9 Hz, 2H) d) 3.66-3.63 (m, 2H) e) 3.40 (s, 3H) f) 1.75-1.56 (m, 2H) g) 0.51-0.44 (m, 2H) h) 0.10 (s, 27H)

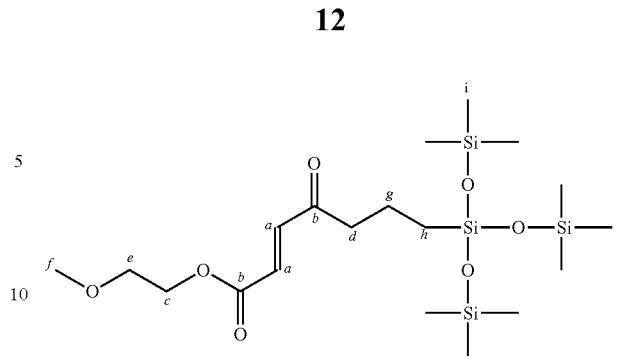

$^{13}$C NMR (CDCl$_3$), δ, ppm a) 165.0, 164.9 b) 134.2, 133.0 c) 70.2 d) 67.5 e) 64.3 f) 59.0 g) 22.6 h) 10.3 i) 1.7

IR (NaCl), cm$^{-1}$ 2960 ($V_{C-H}$), 1727 ($V_{C=O}$), 1645 ($V_{C=C}$), 1255 ($V_{Si-C}$), 1297, 1156 ($V_{C(=O)-O}$), 1060 ($V_{O-Si-O}$)

—Polymerization of Materials for Water-Containing Contact Lenses Using Compound 1—

Examples 1 and 2, and Comparative Examples 1 and 2

Fifty parts by weight of compound 1, 33 parts by weight of N-vinyl pyrrolidone (hereinafter referred to as "NVP"), and 17 parts by weight of 2-hydroxyethyl methacrylate (hereinafter referred to as "2-HEMA") were dissolved by adding 0.3 parts by weight of ethylene glycol di(meth)acrylate as a crosslinking agent, and 0.3 parts by weight of 2,2'-azobisisobutyronitrile as a polymerization initiator. This solution was then poured into a tool made of two glass plates (75 mm×25 mm×2 mm) between which nylon sheet and silicone spacers cut out with a diameter of φ15 and having a thickness of 0.2 mm are sandwiched.

Next, the tool was clipped to prevent leaking, placed in the programmed oven, and heated from room temperature to 60° C. over a period of one hour, held at this temperature for 2 hours, heated to 75° C. over a period of one hour, and held at this temperature further for 2 hours. The tool was then heated further to 90° C. over a period of one hour, held at this temperature for 2 hours, and gradually cooled down to room temperature, thereby producing a polymer film with a thickness of 0.2 mm. The film thus obtained was transparent and hard. This film was hydrated in physiological saline, and its properties were determined according to the following methods. The results are shown in Table 1.

(A) Water Content (% by Weight)

The water content of the film at the temperature of 35° C. was determined based on the following equation:

$$\text{Water Content(\% by weight)} = \{(W-W_0)/W\} \times 100.$$

In the equation, W represents the weight (g) of the test film in the equilibrium state of water content after hydration; and $W_0$ represents the weight (g) of the film in the dried stated, which had been hydrated and then dried in the dry oven.

(B) Oxygen Permeability Coefficient ($Dk_{O_2}$)

As an evaluation of the oxygen permeability, the value calculated by multiplying by $10^{11}$ the oxygen permeability coefficient of the film measured in the following conditions is shown: the film with a thickness of 0.2 mm was measured at 35° C. in the physiological saline using an oxygen transmission rate measurement system manufactured by TSUKUBA RIKASEIKI Co. Ltd. Units: (cm$^2$/sec)·(ml O$_2$/ml·mmHg)

(C) Transparency (%)

As an evaluation of the transparency, the transparency rate (%) of the film in a hydrated state measured at the wavelength of 380 to 780 nm, using UV measuring system manufactured by SHIMADZU CORPORATION is shown.

TABLE 1

|  | Ex. | | Com. Ex. | |
|---|---|---|---|---|
|  | 1 | 2 | 1 | 2 |
| Monomer Composition ratio | | | | |
| Compound 1 | 50 | 50 | | |
| TRIS | | | 50 | 50 |
| NVP | 33 | 50 | 33 | 50 |
| 2-HEMA | 17 | | 17 | |
| Physical Properties | | | | |
| Water Content (%) | 42 | 50 | 40 | 53 |
| $Dk_{0.2}$ | 30 | 32 | 30 | 31 |
| Transparency (%) | 97 | 97 | 3 | 23 |

In Table 1, abbreviations of the names of the monomer components are as follows:

TRIS: Tris(trimethylsiloxy)silylpropyl(meth)acrylate

NVP: N-vinyl pyrrolidone

2-HEMA: 2-hydroxyethyl methacrylate

It can be seen from the results shown in Table 1 that in some combinations with other monomer components, TRIS, a predominant conventional silicone monomer, has a problem of poor transparency in the hydrated state, and in contrast that since compound 1 of the present invention has good transparency, in view of the structure of fumaric acid diester, it shows the effect of using a monomer intramolecularly having both hydrophilic and silicon-containing alkyl groups. With respect to the oxygen permeability, both compounds show high values depending on the content of the silicon monomer.

Examples 3-8 and Comparative Examples 3-7

Films were obtained according to the same method as described in Example 1, except that the compositions of the polymer components were altered as shown in Table 2 (Examples 3 to 8) and in Table 3 (Comparative Examples 3 to 7). The films thus obtained were subjected to the same measurements as in Example 1. The results are shown below in Tables 2 and 3.

TABLE 2

|  | Ex. | | | | | |
|---|---|---|---|---|---|---|
|  | 3 | 4 | 5 | 6 | 7 | 8 |
| Monomer Composition ratio | | | | | | |
| Compound 1 | 50 | 50 | 60 | 70 | 42 | 36 |
| 6FP | | | | | 28 | 24 |
| NVP | 25 | 33 | 27 | 30 | 30 | 40 |
| DMAA | | 17 | | | | |
| 2-HEMA | 25 | | 13 | | | |
| Physical Properties | | | | | | |
| Water Content (%) | 28 | 60 | 31 | 25 | 24 | 40 |
| $Dk_{0.2}$ | 31 | 33 | 29 | 37 | 34 | 29 |

In Table 2, abbreviations of the names of the monomer components are as follows:

6FP: hexafluoroisopropyl(meth)acrylate

NVP: N-vinyl pyrrolidone

DMAA: N,N-dimethylacrylamide

2-HEMA: 2-hydroxyethyl methacrylate

TABLE 3

|  | Com. Ex. | | | | |
|---|---|---|---|---|---|
|  | 3 | 4 | 5 | 6 | 7 |
| Monomer Composition ratio | | | | | |
| NVP | | 40 | 50 | 60 | 70 |
| 2-HEMA | 100 | 60 | 50 | 40 | 30 |
| Physical Properties | | | | | |
| Water Content (%) | 37 | 53 | 61 | 70 | 77 |
| $Dk_{0.2}$ | 9 | 14 | 18 | 20 | 20 |

In Table 3, abbreviations of the names of the monomer components are as follows:

NVP: N-vinyl pyrrolidone

2-HEMA: 2-hydroxyethyl methacrylate

The results shown in Tables 2 and 3 reveal that $Dk_{0.2}$ in the Examples for the present invention was 1.5 fold higher than that of the water content-dependent materials (in Comparative Examples).

Focusing on the water contents and oxygen permeability coefficients, the relationship of these properties are shown in FIG. 1 for Examples 1-8 and Comparative Examples 3-7. The figure shows that as compared to the conventional water content-dependent soft contact lenses, the lens material of the present invention retains a high level of oxygen permeability independently of the water content.

—Synthesis of Compound 2—

A fumaric acid diester (Compound 2) may be obtained according to the following reaction formulae:

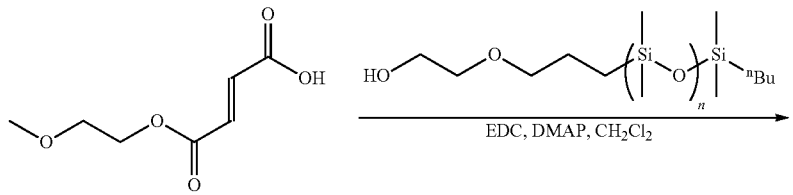

-continued

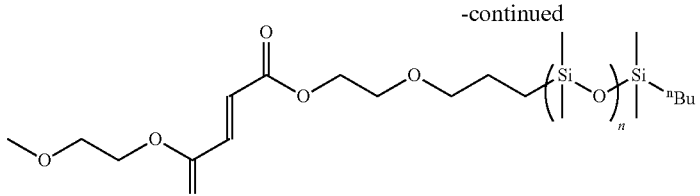

Compound 2

Initially, 3.5 g (20 mmol) of 2-methoxyethyl maleate, 11.3 g (10 mmol) of polyorganosiloxane compound 1 having the structure shown below, and 245 mg (2.0 mmol) of 4-dimethylaminopyridine were dissolved in 40 ml of methylene chloride. To this mixture, 3.9 g (20 mmol) of 1-ethyl-3-(3-dimethylaminopropyl)carbodiimide hydrochloride (hereinafter referred to as "EDC") was added, and the mixture was stirred for 3 hours at room temperature. The reaction mixture was washed in 1N hydrochloric acid, dried over magnesium sulfate, and subjected to vacuum to remove the solvent, followed by purification by silica gel column chromatography (chloroform). Intended Compound 2 was thus obtained. The yield was 95%.

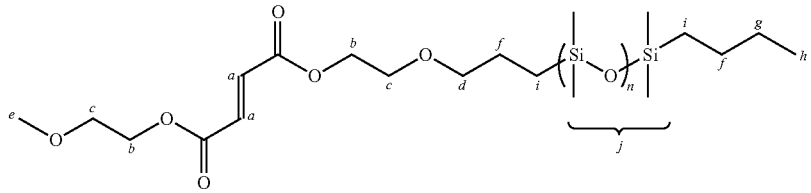

$^1$H- and $^{13}$C-nuclear magnetic resonance spectra of Compound 2 were measured using Model JNMα-400 manufactured by JAPAN ELECTRON OPTICS LABORATORY Co., LTD in deuterated chloroform at 25° C. with 8 cumulative measurements for $^1$H-nuclear magnetic resonance spectrum and 128 cumulative measurements for $^{13}$C-nuclear magnetic resonance spectrum.

The results are as shown below:

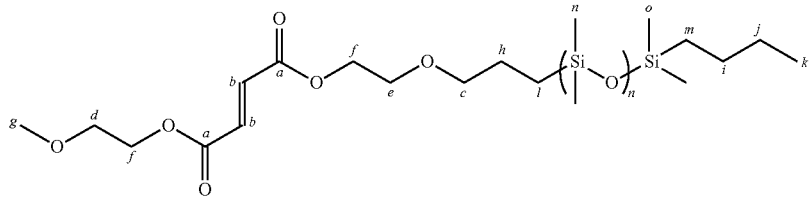

$^1$H NMR (CDCl$_3$), δ, ppm a) 6.92 (s, 2H) b) 4.37-4.32 (m, 4H) c) 3.68-3.62 (m, 4H) d) 3.45-3.41 (m, 2H) e) 3.39 (s, 3H) f) 1.64-1.57 (m, 4H) g) 1.33-1.25 (m, 2H) h) 0.90-0.85 (m, 3H) i) 0.55-0.49 (m, 4H) j) 0.07 (s, many)

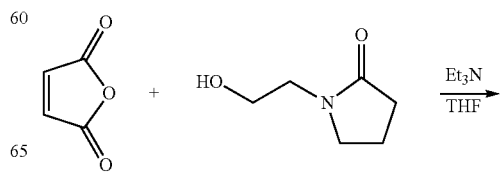

$^{13}$C NMR (CDCl$_3$), δ, ppm a) 164.8 b) 133.7, 133.5 c) 74.1 d) 70.2 e) 68.2 f) 64.5, 64.2 g) 58.9 h) 26.3 i) 25.4 j) 23.4; 23.3, 23.2 k) 17.9 l) 14.0 m) 13.7 n) 1.9, 1.8, 1.6, 1.5, 1.1, 1.0, 0.5, 0.4, 0.3 o) 0.1

IR (NaCl), cm$^{-1}$ 2962 ($V_{C-H}$), 1729 ($V_{C=O}$), 1646 ($V_{C=C}$), 1260 ($V_{Si-C}$), 1296, 1091 ($V_{C(=O)-O}$), 1025 ($V_{O-Si-O}$)

—Synthesis of Compound 3—

A fumaric acid diester (Compound 3) may be obtained according to the following reaction formulae:

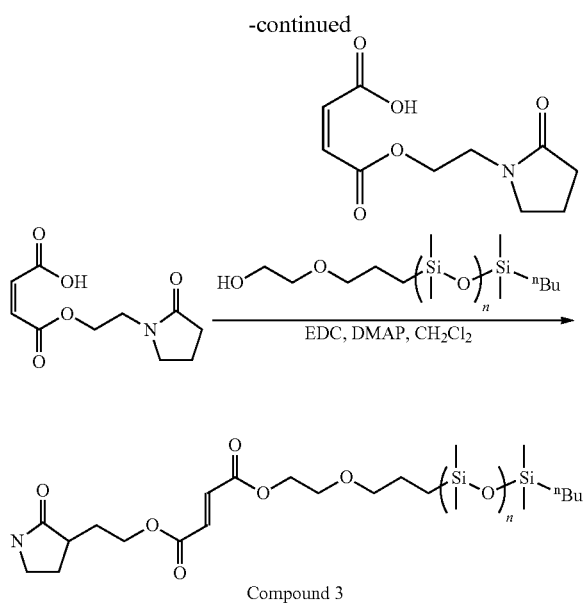

The synthesis was initiated by mixing 10 g (102 mmol) of maleic acid anhydride with 13 g (102 mmol) of 1-(2-hydroxyethyl)-2-pyrrolidinone were mixed, and the mixture was dissolved by adding 20 ml of THF. Then, 0.5 ml of Et₃N was added to the mixture and allowed to react for 2 hours at room temperature. The intended product was isolated as a precipitate from the reaction solution by filtration. The yield was 96%.

Then, 1.0 g (4.4 mmol) of 2-(2-oxopyrrolidinyl)ethyl maleate thus obtained, 2.5 g (2.2 mmol) of polyorganosiloxane compound 1 and 54 mg (0.44 mmol) of 4-dimethylaminopyridine were dissolved in 5 ml of methylene chloride. To this mixture, 0.84 g (4.4 mmol) of EDC was added, and the mixture was stirred for 84 hours at room temperature. The reaction mixture was washed in 1N hydrochloric acid, dried over magnesium sulfate, and subjected to vacuum to remove the solvent, followed by purification by silica gel column chromatography (methylene chloride/ethyl acetate=10/1). Intended Compound 3 was thus obtained. The yield was 49%.

$^1$H- and $^{13}$C-nuclear magnetic resonance spectra of Compound 3 were measured using Model JNMα-400 manufactured by JAPAN ELECTRON OPTICS LABORATORY Co., LTD in deuterated chloroform at 25° C. with 8 cumulative measurements for 1H-nuclear magnetic resonance spectrum and 128 cumulative measurements for $^{13}$C-nuclear magnetic resonance spectrum.

The results are as shown below:

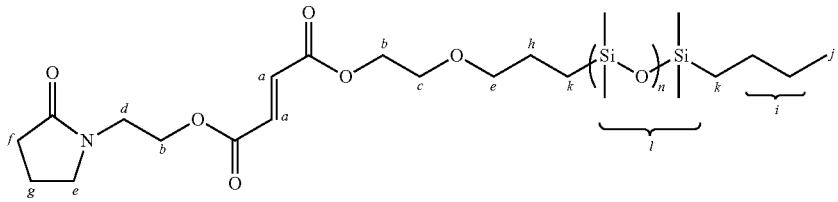

$^1$H NMR (CDCl₃), δ, ppm a) 6.90 (s, 2H) b) 4.36-4.32 (m, 4H) c) 3.68 (t, J=4.7 Hz, 2H) d) 3.60 (t, J=5.4 Hz, 2H) e) 3.50-3.41 (m, 4H) f) 2.38 (t, J=8.3 Hz, 2H) g) 2.07-2.01 (m, 2H) h) 1.65-1.58 (m, 2H) i) 1.33-1.25 (m, 4H) j) 0.88 (t, J=6.9 Hz, 3H) k) 0.55-0.49 (m, 4H) l) 0.08-0.05 (m, many)

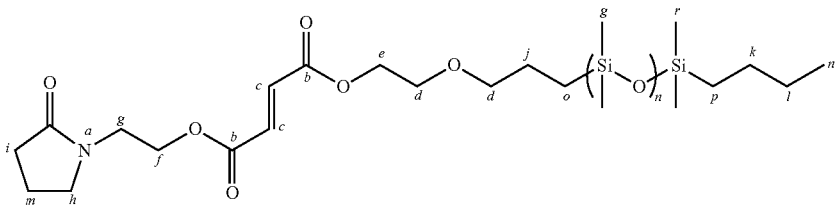

$^{13}$C NMR (CDCl₃), δ, ppm a) 175.3 b) 164.6, 164.4 c) 133.9, 133.6 d) 68.2 e) 64.5 f) 62.7 g) 47.9 h) 41.5 i) 30.5 j) 26.2 k) 25.3 l) 23.3 m) 18.0 n) 17.8 o) 14.0 p) 13.7 q) 1.6, 1.5, 1.0, 0.9, 0.5, 0.4 r) 0

IR (NaCl), cm$^{-1}$ 2961, 2872 ($V_{C-H}$), 1726 ($V_{C=O}$), 1693 ($V_{C=C}$), 1294 ($V_{C(=O)-O}$), 1259 ($V_{Si-C}$), 1025 ($V_{O-Si-O}$)

In addition, Compound 4 as shown below was obtained using the same method as described above, except that polyorganosiloxane compound 2, which has the following structure, was used instead of polyorganosiloxane compound 1.

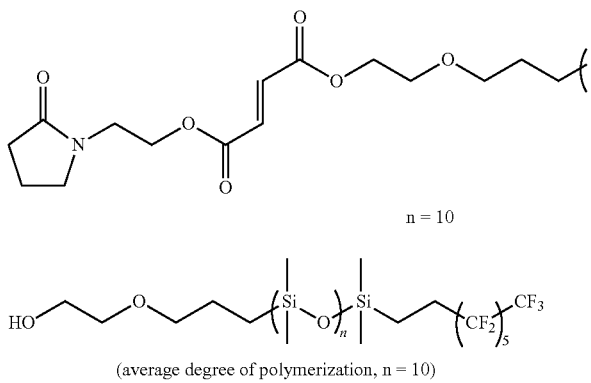

Compound 4 n = 10

Polyorganosiloxane compound 2

(average degree of polymerization, n = 10)

Examples 9-23

Compounds 2 to 4, obtained as described above, were used to prepare the compositions of the copolymer components as shown in Tables 4 to 7. The preparations were polymerized using the methods described in Examples 1 and 2 under the following temperature conditions: they were heated from room temperature to 90° C. over a period of 30 minutes, held at this temperature for 1 hour, then heated to 110° C. over a period of 30 minutes, held at this temperature for 1 hour, and gradually cooled down to room temperature. Polymer films with a thickness of 0.2 mm were thus obtained. The polymer films obtained were hydrated in distilled water, and their properties were tested. The results are shown in Tables 4 to 6.

Compound 3 was formulated in the copolymer compositions shown in Table 5, dissolved by adding 0.3 parts by weight of ethylene glycol dimethacrylate as a crosslinking agent and 0.3 parts by weight of 2,2'-azobisisobutyronitrile as a polymerization initiator, and then poured into a glass tube (φ18×200 mm), which was stoppered tightly. Subsequently, the tube was incubated overnight (about 16 hours) at 35° C. in the circulation constant-temperature bath, and held at 45° C. for 4 hours and then at 55° C. for 4 hours. And then, the tube was placed in the programmed oven, and heated to 60° C. over a period of 30 minutes, held at this temperature for 1 hour, subsequently heated to 90° C. over a period of 30 minutes, held at this temperature for 1 hour, then heated to 110° C. over a period of 30 minutes, heated at this temperature for 1 hour, and gradually cooled down to room temperature.

The polymer obtained was removed from the tube, and subjected to heat treatment for 30 minutes at 110° C., resulting in a transparent and undistorted bar-shaped polymer.

Since this bar-shaped polymer was sufficiently hard to allow cutting, it was formed into a contact lens by cutting, and then hydrated in physiological saline, resulting in a lens of good quality. The physical property values obtained from this bar-shaped polymer were equivalent to the results shown in Table 5.

TABLE 4

| | Ex. | | | | | | | |
|---|---|---|---|---|---|---|---|---|
| | 9 | 10 | 11 | 12 | 13 | 14 | 15 | 16 |
| Monomer Composition ratio | | | | | | | | |
| Compound 2 | 20 | 25 | 20 | 20 | 10 | 15 | 20 | 10 |
| TRIS | 30 | 25 | 35 | 20 | 50 | 45 | 40 | 50 |

TABLE 4-continued

| | Ex. | | | | | | | |
|---|---|---|---|---|---|---|---|---|
| | 9 | 10 | 11 | 12 | 13 | 14 | 15 | 16 |
| FM7711 | | | | 15 | | | | |
| NVP | 25 | 25 | 20 | 20 | 20 | 20 | 20 | 15 |
| DMAA | 25 | 25 | 25 | 25 | 20 | 20 | 20 | 25 |
| Physical Properties | | | | | | | | |
| Water Content (%) | 53 | 53 | 49 | 28 | 40 | 43 | 45 | 40 |
| $Dk_{0.2}$ | 37 | 38 | 32 | 34 | 46 | 47 | 52 | 41 |
| Transparency (%) | 98 | 99 | 98 | 99 | 96 | 93 | 96 | 97 |

TABLE 5

| | Ex. | | | |
|---|---|---|---|---|
| | 17 | 18 | 19 | 20 |
| Monomer Composition ratio | | | | |
| Compound 3 | 15 | 20 | 25 | 40 |
| TRIS | 35 | 30 | 25 | 10 |
| NVP | 25 | 25 | 25 | 25 |
| DMAA | 25 | 25 | 25 | 25 |
| Physical Properties | | | | |
| Water Content (%) | 60 | 61 | 63 | 54 |
| $Dk_{0.2}$ | 27 | 32 | 48 | 34 |
| Transparency (%) | 98 | 98 | 96 | 98 |

TABLE 6

| | Ex. | | |
|---|---|---|---|
| | 21 | 22 | 23 |
| Monomer Composition ratio | | | |
| Compound 4 | 15 | 20 | 25 |
| TRIS | 35 | 30 | 25 |
| NVP | 25 | 25 | 25 |
| DMAA | 25 | 25 | 25 |
| Physical Properties | | | |
| Water Content (%) | 56 | 54 | 50 |
| $Dk_{0.2}$ | 33 | 38 | 48 |
| Transparency (%) | 97 | 97 | 96 |

In Tables 4-6, the abbreviations of the names of the monomer components are as follows:
TRIS: Tris(trimethylsiloxy)silylpropyl methacrylate
FM7711: α,ω-(3-methacryoxypropyl)polydimethylsiloxane, Chisso Co.;
average molecular weight: 1000
NVP: N-vinyl pyrrolidone
DMAA: N,N-dimethylacrylamide Comparative Examples 8-10

Polymer films with a thickness of 0.2 mm were obtained as described in Examples 9-23, except that the compositions of the copolymer components were altered as shown in Table 7. The films obtained were hydrated in distilled water, and their physical properties were tested. The results are shown in Table 7.

TABLE 7

|  | Com. Ex. | | |
| --- | --- | --- | --- |
|  | 8 | 9 | 10 |
| Monomer Composition ratio | | | |
| FM7711 |  | 20 | 25 |
| TRIS | 50 | 30 | 25 |
| NVP | 25 | 25 | 25 |
| DMAA | 25 | 25 | 25 |
| Physical Properties | | | |
| Water Content (%) | 49 | 31 | 26 |
| $Dk_{0.2}$ | 27 | 28 | 32 |
| Transparency (%) | 97 | 97 | 99 |

In Table 7, the abbreviations of the names of the monomer components are as follows:
FM7711: α,ω-(3-methacryoxypropyl)polydimethylsiloxane, Chisso Co.; average molecular weight: 1000
TRIS: Tris(trimethylsiloxy)silylpropyl methacrylate
NVP: N-vinyl pyrrolidone
DMAA: N,N-dimethylacrylamide The results shown in Tables 4-6 reveal that the film obtained according to the present invention exhibits good transparency in the hydrated state. The film showed higher oxygen permeability as compared to widely used conventional polydimethylsiloxane methacrylates such as shown in Comparative Examples 9 and 10 in Table 7. The $Dk_{0.2}$ value of the film of the present invention was 1.5 to 2.5 fold higher than that of the water content-dependent materials (Comparative Examples 3-7).

In addition, when predominantly used conventional silicone monomers, such as TRIS and polydimethylsiloxane methacrylates, were used, water content tends to markedly reduced depending on the amount of these monomers used (Comparative Examples 8-10). In contrast, from fact that when Compounds 2 and 3 were used, the water content was slightly increased depending on the amount of Compounds 2 and 3, it can be seen that the effect of using a monomer that intramolecularly has both hydrophilic and silicon-containing alkyl groups in the structure of the fumaric acid diester of the present invention has been shown. With respect to Compound 4, although the water content was slightly reduced depending on the amount of this compound used, it can be seen from the comparison between Example 23 and Comparative Example 10 that the use of Compound 4 particularly contributes to the retention of high oxygen permeability and water content.

What is claimed is:
1. A fumaric acid derivative having a hydrophilic group (R) and a silicon-containing alkyl group, which is represented by formula (1):

$$R-Y_1-\overset{\overset{O}{\|}}{C}-\underset{\underset{O}{\|}}{\overset{CH}{\underset{HC}{\|}}}-C-O-Y_2-\overset{X_1}{\underset{X_3}{\overset{|}{Si}}}-X_2 \quad (1)$$

wherein $Y_1$ is O or $NR_1$ ($R_1$ is selected from the group consisting of hydrogen, $C_{1-3}$ alkyl and aryl);
R is selected from the group represented by the following formula:

$$-(CH_2)n-N\underset{O}{\overset{}{\bigcirc}}, \quad -CH_2CH_2-\overset{CH_3}{\underset{CH_3}{\overset{|}{N^+}}}-O^-, \quad or$$

($n$ is an integer from 1 to 3)

$$-CH_2CH_2-\overset{CH_3}{\underset{CH_3}{\overset{|}{N^+}}}-CH_2COO^-$$

$Y_2$ is selected from linear or branched $C_{3-10}$ alkylene, phenylene, cyclohexylene, $-(CH_2CH_2O)_o-CH_2CH_2CH_2-$ (o is an integer from 1 to 10), or a group represented by any one of the following formulae:

$$-CH_2-\underset{}{\bigcirc}-CH_2-, \quad -CH_2-\underset{}{\bigcirc}-CH_2-,$$

$$-\underset{}{\bigcirc}-CH_2-\underset{}{\bigcirc}-,$$

$$-\underset{}{\bigcirc}-CH_2-\underset{}{\bigcirc}-$$

$X_1$, $X_2$ and $X_3$ are independently selected from the group consisting of methyl, trimethylsiloxy, and organosiloxy with 18 Si atoms or less.

2. An ophthalmic lens obtained by polymerizing a composition comprising the fumaric acid derivative of claim 1.

3. The ophthalmic lens of claim 2, formed from a copolymer polymerized from 10 to 80% by weight of the fumaric acid derivative and 90 to 20% by weight of another copolymerizable component.

4. The ophthalmic lens of claim 3, wherein said another copolymerizable component is one or more polymerizable components selected from the group consisting of fumaric acid diesters other than the fumaric acid derivative, fumaric acid diamides, fumaric acid amide esters, N-vinyl lactams, N,N-dialkyl(meth)acrylamides, and hydroxyethyl (meth)acrylic acid esters.

* * * * *